United States Patent [19]

Swann et al.

[11] Patent Number: 5,760,084

[45] Date of Patent: Jun. 2, 1998

[54] RARγ-SPECIFIC RETINOBENZOIC ACID DERIVATIVES

[75] Inventors: R. Thomas Swann; Daniel Smith, both of Hamden, Conn.; Kenneth M. Tramposch, E. Amherst, N.Y.; Fred Christopher Zusi, Hamden, Conn.

[73] Assignee: Bristol-Myers Squibb Company, Princeton, N.J.

[21] Appl. No.: 724,979

[22] Filed: Oct. 4, 1996

Related U.S. Application Data

[62] Division of Ser. No. 467,429, Jun. 6, 1995, Pat. No. 5,624,957.

[51] Int. Cl.$^6$ .................................................. A61K 31/245
[52] U.S. Cl. ............................................................ 514/563
[58] Field of Search .................................... 514/535, 563

[56] References Cited

FOREIGN PATENT DOCUMENTS

| | | |
|---|---|---|
| 92/06948 | 4/1992 | Australia . |
| 92/3470 | 5/1992 | South Africa . |
| WO 93/03713 | 3/1993 | WIPO . |

OTHER PUBLICATIONS

Multiplicity generates diversity in the retinoic acid signalling pathways, Mark Leid et al, *Trends in Biochemical Sciences*, 17: 427–433, 1995.

Rudd, et al., Cancer Lett. (Shannon, Irel.) 73(1), 41–9, 1993.

Taylor J. of Craniofacial Genetics and developmental Biology 15 (1) 13 Abstract, 1995.

*Primary Examiner*—Robert Gerstl
*Attorney, Agent, or Firm*—David M. Morse

[57] ABSTRACT

Retinoid-like activity is exhibited by compounds of the formula

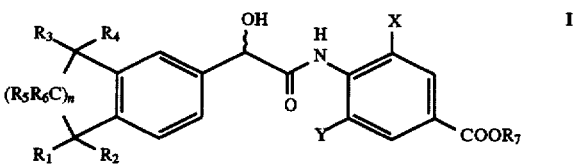

wherein X is F, Cl, OH or $CH_3$, Y is H or F, $R_1$–$R_6$ are each independently hydrogen or $C_1$–$C_6$ alkyl, n is an integer of 1 to 4 and $R_7$ is hydrogen or a carboxyl-protecting group, and pharmaceutically acceptable salts thereof. The compounds of the formula I selectively interact with the retinoic acid subtype RARγ and have been found to lack the liver toxicity associated with systemic administration of non-relative retinoids.

5 Claims, 1 Drawing Sheet

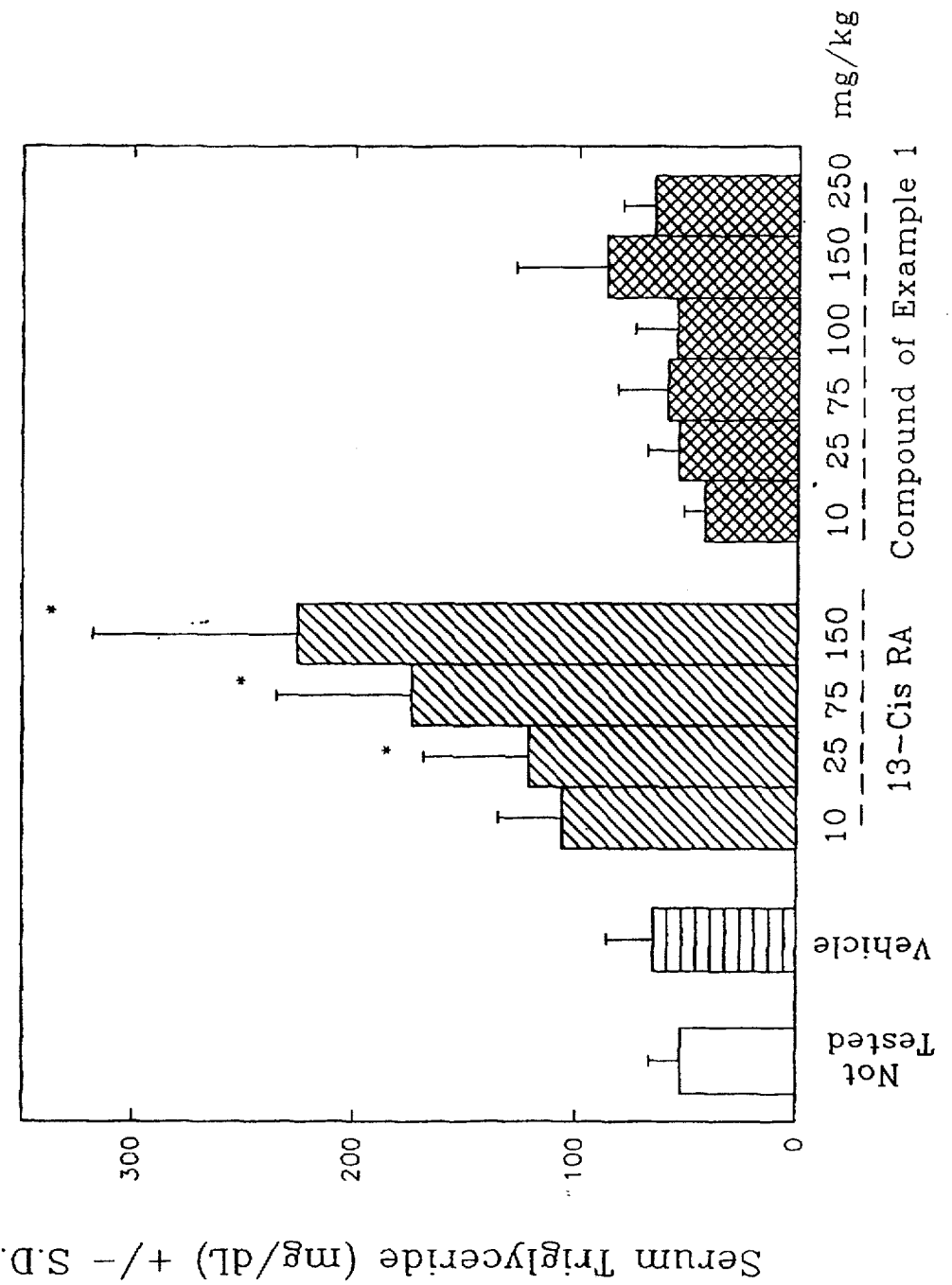

RARγ-SPECIFIC RETINOBENZOIC ACID DERIVATIVES

CROSS-REFERENCE TO RELATED APPLICATION(S)

This is a division fo U.S. patent application Ser. No. 08/467,429 filed Jun. 6, 1995, now U.S. Pat. No. 5,624,957.

BACKGROUND OF THE INVENTION

1. Field of the Invention

The present invention relates to a novel series of retinobenzoic acid derivatives having retinoid-like activity. More specifically, the novel compounds of the present invention are specific agonists of RARγ. They are useful, for example, in treatment of a wide variety of dermatological conditions, e.g. acne, psoriasis, eczema and photoaging of skin, in treatment of corneopathies in opthalmology, in treatment of degenerative diseases of connective tissue, i.e. arthritis, and in the treatment of malignancies.

2. Description of the Related Art

Vitamin A is an essential nutrient for most mammalian species. It is normally supplied in the diet as retinol:

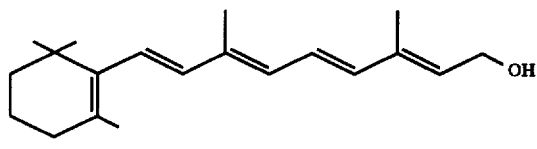

Retinol

Adequate levels of this nutrient are required for normal growth, vision and reproduction. It has been discovered that most of the effects on cellular growth and differentiation (but not the effects on vision) are mediated through the oxidized metabolite, retinoic acid:

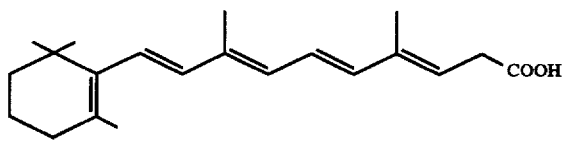

Retinoic acid

Based on the structure of retinoic acid, many analogs (termed "retinoids") have been synthesized over the years as drugs for various applications. There is a vast and growing scientific literature on the chemistry, biology and clinical uses of the retinoids.

A few retinoids are already in clinical use in the treatment of dermatological diseases such as acne and psoriasis. For example, isotretinoin is used clinically for oral therapy of severe acne:

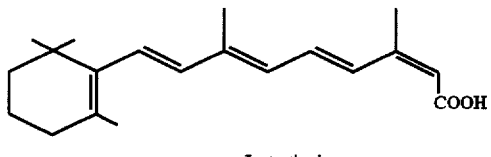

Isotretinoin

Retinoids have been shown to have a variety of medical uses in conditions such as acne, psoriasis, cancer, and the repair of photoaging of the skin. Despite such beneficial properties, use of the available retinoids is associated with a number of significant side effects. For example, systemic use of clinically available retinoids such as isotretinoin causes an elevation in triglyceride levels in about ⅓ of the patients treated, thus requiring periodic invasive monitoring.

The molecular basis for the activity of retinoic acid has been the subject of considerable research over the years. A major breakthrough came in recent years with the discovery of the nuclear retinoic acid receptors (RARs). These are proteins located in the cell nucleus, members of the steroid/thyroid hormone receptor superfamily. Retinoic acid binds to these proteins. Then the ligand/protein complex binds to DNA and transcription of specific genes is activated (or depressed). Genes important to cell proliferation and differentiation are among those regulated.

Three forms of the RARs have been described and termed RARα, RARβ and RARγ. These receptors differ in their tissue distribution and in their times of occurrence in developing fetuses, but to date no definite difference in their functions has been observed. It has been theorized that the development of retinoids which specifically bind to and activate individual receptor subtypes would result in compounds with an improved therapeutic index compared to clinically used retinoids, which are not selective for one type over another, e.g. see WO 93/03713 and Leid, et al. in *Trends in Biochemical Sciences* 1992, 17, 427–433.

With regard to the retinobenzoic acid derivatives provided by the present invention, applicants are aware of the following references disclosing structurally related compounds.

U.S. Pat. No. 5,128,479 discloses retinoids of the formula

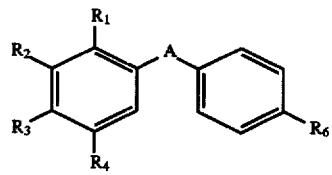

where A may be CHOH—CH$_2$—X or C(=O)CH$_2$X, with X=N, O or S and R$_2$ and R$_3$ are defined to make up the fragment

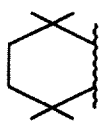

The closest of the exemplified compounds appears to be

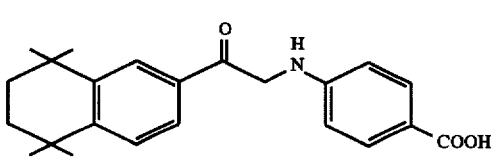

In South African Patent 92/3470, there are disclosed compounds of the following generic structure:

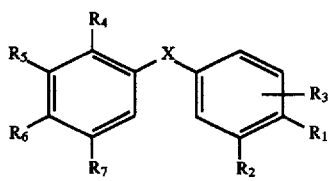

where $R_1$ may be COOH, $R_2$ is OH or O-acyl, $R_3$ is H,OH or O-acyl, $R_5$ and $R_6$ may be $-C(CH_3)_2CH_2CH_2C(CH_3)_2-$ and X is a variety of 3-atom fragments. The closest exemplified compound is

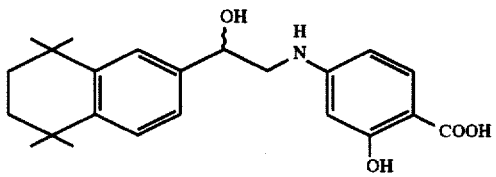

In Australian Patent No. 646314 (corresponding to WO 92/6948) are disclosed compounds of the same general structure as that of South African Patent 92/3470, but with additional exemplified compounds such as:

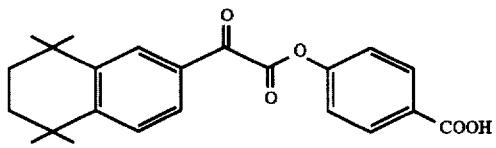
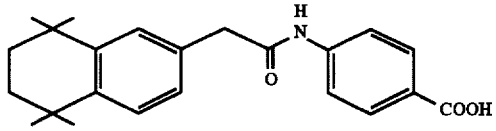
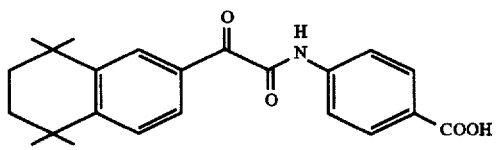
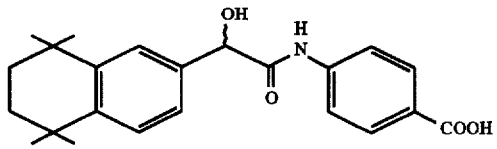
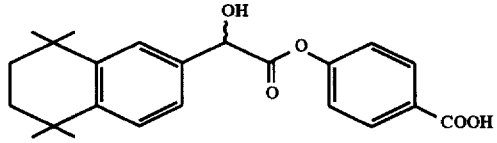
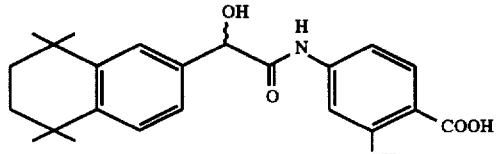

The claimed utility for retinoid compounds, including those mentioned above, is for the treatment of dermatological afflictions/disorders of keratinization, for inflammatory or allergic conditions (including the degeneration of connective tissue, i.e. arthritis), tumors, treatment of atopy (topical or systemic), psoriatic arthritis or corneopathies in opthalmology.

The compounds of the present invention may be structurally distinguished from prior art retinobenzoic acid derivatives by the mandatory inclusion of a small substituent (F, Cl, OH or $CH_3$) at the 3-position of the terminal benzene ring (that containing the carboxyl group). Applicants have unexpectedly found that retinoid compounds which specifically activate the RARγ subtype, particularly the retinobenzoic acidderivatives provided by the present invention, have a significant advantage over non-selective retinoids in lacking the liver toxicity associated with systemic use of such retinoids.

SUMMARY OF THE INVENTION

The novel retinobenzoic acids provided by the present invention have the general formula

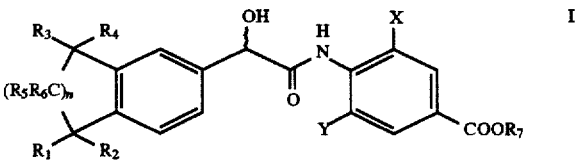

wherein X is F, Cl, OH or $CH_3$, Y is H or F, $R_1$–$R_6$ are each independently hydrogen or $C_1$–$C_6$ alkyl, n is an integer of 1 to 4 and $R_7$ is hydrogen or a carboxyl-protecting group, or a pharmaceutically acceptable salt thereof. The compounds of formula I have retinoid-like activity and are thus useful in the treatment of skin disorders such as acne, Darier's disease, psoriasis, icthyosis, eczema, atopic dermatitis and epithelial cancers. They are also useful in the treatment of arthritic diseases and other immunological disorders (e.g. lupus erythematosus), in promoting wound healing, in treating dry eye syndrome and in treatment of the effects of sun damage to skin, i.e. photoaging. They also are useful in the treatment of various malignant tumors and premalignant skin lesions, e.g. actinic keratoses.

Also included in the invention are processes for preparing the compounds of formula I and pharmaceutical compositions containing said compounds in combination with pharmaceutically acceptable carriers or diluents.

In another aspect of the present invention, there is provided a method for treating a mammalian subject for dermatological, rheumatic, antitumor, respiratory or opthalmological conditions known to be affected by retinoid derivatives without inducing hypertriglyceridemia which comprises systemically administering a therapeutically effective amount of a retinoid compound which is a specific agonist of RARγ.

BRIEF DESCRIPTION OF THE DRAWINGS

FIG. 1 shows the effects of the compound of Example 1 on rat serum triglyceride levels.

DETAILED DESCRIPTION

As noted above, the compounds of formula I differ from prior art retinoid derivatives of the general type by the mandatory presence of a small substituent (F, Cl, OH or $CH_3$) at the 3-position of the benzene ring containing the carboxyl moiety. Applicants have discovered that compounds lacking such a 3-substituent or having one which is larger than those specified in formula I are either non-selective or inactive in the transactivation assay used to determine selectivity of retinoids to RAR receptor subtypes. The compounds of the present invention may optionally contain a fluorine substituent at the 5-position of this same benzene ring.

The term "$C_1$–$C_6$ alkyl" as used herein refers to straight or branched chain alkyl groups having from 1 to 6 carbon atoms, e.g. methyl, ethyl, propyl, isopropyl, butyl, isobutyl, t-butyl, amyl, hexyl, and the like.

Preferably these groups contain from 1–4 carbon atoms and, most preferably, they contain 1 or 2 carbon atoms.

The "n" substituent in formula I may be an integer of from 1 to 4 and is preferably 1 (indane series) or 2 (naphthyl series). The mostpreferred compounds are those wherein n is 2. Of this group, it is preferred that $R_1$, $R_2$, $R_3$ and $R_4$ are each methyl and $R_5$ and $R_6$ are both hydrogen.

A preferred embodiment comprises compounds of the formula

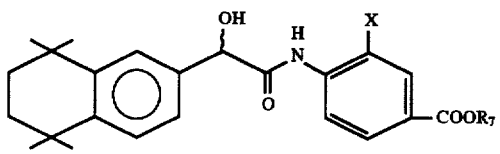

wherein X and $R_7$ are as defined above, or pharmaceutically acceptablesalts thereof.

Another preferred embodiment comprises compounds of the formula

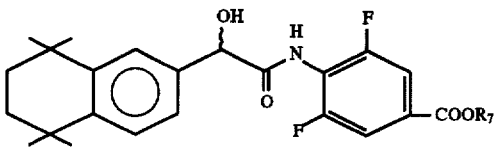

wherein $R_7$ is hydrogen or a carboxyl-protecting group, or a pharmaceutically acceptable salt thereof. Preferred are the compounds where $R_7$ is hydrogen or a physiologically hydrolyzable ester group, or apharmaceutically acceptable salt thereof. A most preferred embodiment comprises the compound where $R_7$ is hydrogen, or a pharmaceutically acceptable salt thereof.

The compounds of the present invention may contain chiral centers and are generally produced as diastereomer mixtures or racemates. The diastereomers can be separated, for example, by differences in solubility or by column chromatography, and isolated in pure form. Pure enantiomers can be resolved from the pairs of enantiomers and the mixtures thereof (racemates).

The compounds of the present invention containing an acidic hydrogen may be converted with bases in a conventional manner into a pharmaceutically acceptable salt. Examples of suitable salts are ammonium and alkali metal salts, especially of sodium, potassium and lithium, and alkaline earth metal salts, especially calcium or magnesium, as well as salts with suitable bases such as with lower alkylamines, e.g. methylamine, ethylamine or cyclohexylamine, or with substituted lower alkylamines such as diethanolamine or triethanolamine and with piperidine or morpholine.

The carboxyl-protecting group $R_7$ is intended to include readily removable ester groups which have been employed to block a carboxyl group during the reaction steps used to prepare the compounds of the present invention and which can be removed by methods which do not result in any appreciable destruction of the remaining portion of the molecule, e.g. by chemical or enzymatic hydrolysis, treatment with chemical reducing agents under mild conditions, irradiation with ultraviolet light or catalytic hydrogenation. Examples of such protecting groups include benzhydryl, p-nitrobenzyl, 2-naphthylmethyl, allyl, benzyl, trichloroethyl, silyl such as trimethylsilyl, phenacyl, acetonyl, o-nitrobenzyl, 4-pyridylmethyl and $C_1$–$C_6$ alkyl such as methyl, ethyl or t-butyl. Included within such protecting groups are those which are hydrolyzed under physiological conditions such as pivaloyloxymethyl, acetoxymethyl, phthalidyl, indanyl, α-acetoxyethyl, α-acetoxybenzyl, p-methoxybenzyl, αα-pivaloyloxyethyl, and methoxymethyl. Compounds of formula I wherein $R_7$ is a physiologically removable protecting group areuseful directly as therapeutic agents. Compounds where $R_7$ is not physiologically removable are useful intermediates which can be easily converted to the active form by conventional deblocking procedures well-known to those skilled in the art.

The compounds of the present invention may be made, for example, according to the reaction sequence illustrated below:

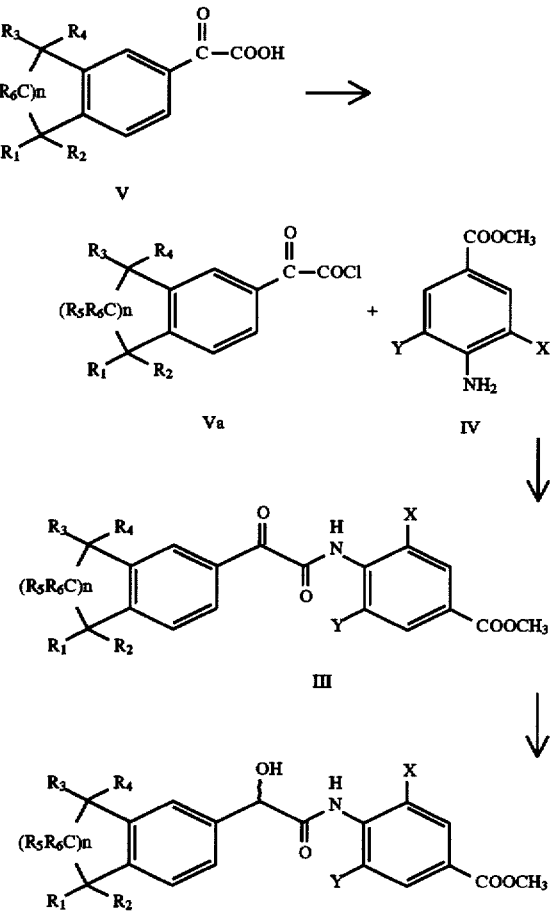

-continued

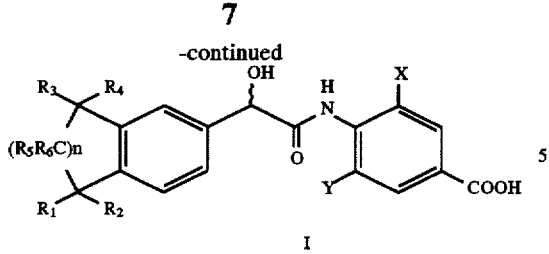

I

To elaborate, keto acid V is converted by known methods (e.g. treatment with thionyl chloride or oxalyl chloride) into the corresponding acid halide, e.g. acid chloride Va, in a suitable inert solvent such as tetrahydrofuran, chloroform or dichloromethane. Acid halide Va is then reacted with the appropriate substituted p-aminobenzoate ester V, also in a suitable inert solvent such as ethyl acetate, chloroform or tetrahydrofuran, to give keto-amide III. The reaction may be accelerated by using a suitable acid scavenger such as triethylamine or dimethylaminopyridine. Starting materials V and IV are ither known in the literature or may be readily made by methods known in the literature. Intermediate III is reduced to hydroxy-amide II with any mild reducing agent, e.g. sodium borohydride, and the carboxyl protecting group, illustrated here by the methyl ester, is cleaved, e.g. by use of sodium or potassium hydroxide in methanol solution, to give the desired retinoid I. It will be understood that other conventional carboxyl-protecting groups may be employed in the synthesis of intermediate V and that such protecting groups may be similarly cleaved by methods well-known to those skilled in the art.

Compounds I may be converted to pharmaceutically acceptable salts by methods known in the art. Similarly, they may be converted to physiologically hydrolyzable esters as indicated above.

As noted above, the compounds of the present invention have retinoid-like activity and can, therefore, be used for the treatment of dermatological, rheumatic, antitumor, respiratory and opthalmological conditions known to be affected by retinoid derivatives. For example, the compounds may be used for the treatment of:

- dermatological conditions linked to a disorder of keratinisation involving differentiation and proliferation, e.g. in treating acne vulgaris, comedonic or polymorphic acne, nodulocystic acne, acne conglobata, senile acne and secondary acnes such as solar, drug and occupational acne;
- for treating other types of keratinisation disorders such as ichthyoses, ichthyosiform states, Darier's disease, palmoplantar keratoderma, leucoplakia and leucoplakiform states, and lichenplanus;
- for treating dermatological conditions linked to a keratinisation disorder with an inflammatory and/or immunoallergic component, e.g. all forms of psoriasis, whether cutaneous, mucosal or ungual, and psoriatic rheumatism, or alternatively, cutaneous atopy, such as eczema, or respiratory atopy;
- for treating dermal or epidermal proliferations, whether benign or malignant, including those of viral origin, such as common warts, flat warts and epidermodysplasia verruciformis;
- for treatment of other dermatological disorders such as vesicular dermatoses and collagen diseases;
- for treatment of certain opthalmological disorders, in particular corneopathies;
- for prophylaxis or treatment of skin aging, both light induced (photoaging) and that occurring with the passage of time;
- for preventing or treating the stigmata of epidermal and/or dermal atrophy induced by local or systemic corticosteroids, or any other form of cutaneous atrophy;
- for treatment of malignant tumors;
- for treatment of premalignant skin lesions such as actinic keratosis;
- for rheumatic illnesses, especially those of an inflammatory or degenerative kind which attack the joints, muscles, tendons and other parts of the motor apparatus, e.g. rheumatic arthritis;
- for promoting cicatrisation; and
- for combating disorders of sebaceous function, such as seborrhea of acne or simple seborrhea.

Dermatological activity of the compounds, for example in the treatment of acne, psoriasis and photoaging, can be demonstrated by the comedolytic activity and the ability to reduce the number of cysts in the rhino mouse model, e.g. as described in Example 2 of U.S. Pat. No. 5,086,060. When representative compounds of the present invention were tested using that same procedure, the $ED_{30}$ (the concentration producing a 30% reduction in the rhino mouse utriculi) values calculated by interpolation of the regression lines of the log concentration-percent reduction plots were as follows:

| The Effect of Compounds on Rhino Mouse Utriculi Diameter | |
|---|---|
| Compound of Ex. No. | $ED_{30}$ (mM) |
| 8 | 1.05 |
| 1 | 0.155 |
| 7 | (32% at 16.5 mM) |
| Retinoic acid (reference) | 0.02 |

Receptor Transactivation

The transactivation assay measures the ability of a retinoid to activate a reporter gene in the presence of one of the retinoic acid receptor subtypes ($\alpha$, $\beta$, or $\gamma$). Activation of just one receptor and failure to activate another is the basis for selectivity/specificity. In our definitions, "selectivity" means that the compound preferentially activates one receptor but also activates at least one other at a higher concentration and "specificity" means that the compound activates only one receptor in the concentration range tested. The details of the receptor-based transactivation assay are disclosed in the literature, e.g. see Nature 1988, 332, 85C–853.

In the retinoid transactivation assay, HeLa cells are co-transfected with DNA encoding RAR $\alpha$, $\beta$, or $\gamma$, and an RAR-responsive CAT (chloramphenicol acetyltransferase) reporter gene. Retinoid efficacy is measured by the concentration of induced CAT gene product as determined by ELISA assay. Retinoic acid (RA) is used as a reference compound. The dosage at which retinoic acid (RA) induction is half the maximal level is termed the $EC_{50}$. The mean $EC_{50}$ value for each of the receptors is calculated using a computer generated induced-fit program. The following table reports the ratios of a test compound's $EC_{50}$ for a given receptor to the $EC_{50}$ of retinoic acid for the same receptor:

TRANSACTIVATION RATIO

| Example # | α | β | γ |
|---|---|---|---|
| 1 | N.A. | * | 3.8 |
| 2 | 66.7 | 50 | 6.7 |
| 3 | N.A. | N.A. | N.A. |
| 4 | N.A. | N.A. | N.A. |
| 5 | N.A. | N.A. | N.A. |
| 6 | N.A. | N.A. | 13.3 |
| 7 | N.A. | N.A. | 40 |
| 8 | N.A. | N.A. | 66.7 |
| 9 | N.A. | N.A. | N.A. |
| 10 | N.A. | N.A. | N.A. |
| Retinoic acid | 1 | 1 | 1 |

*slight activity — less than 35% maximum transactivation at highest dose tested ($10^{-6}$M).

Explanation of Transactivation Results

In absolute terms, the $EC_{50}$ for retinoic acid varies for given receptors, but is usually in the range of $10^{-9}$M (nanomolar range). "N.A." means that the compound had no transactivation at any dose tested (up to $10^{-6}$M). For the 3'-F compound (Example 1) tested against the beta receptor, there was non-zero (measurable) transactivation at the highest dose tested, but it did not reach 35% of the retinoic acid maximum.

Test compounds included representative compounds of the present invention, i.e. compounds of Examples 1, 6, 7, and 8). For comparative purposes, also included are a structurally related literature compound (compound of Example 2 having no 3-substituent on the phenyl ring) and several structurally related compounds previously prepared by applicants (compounds of Examples 3–5, 9 and 10). As can be seen, the compounds of the present invention are specific agonists of the RARγ receptor subtype, whereas the comparison compounds are either non-selective or inactive.

Clinically available systemic retinoids, as noted above, cause an elevation in triglyceride levels (hypertriglyceridemia) in about ⅓ of the patients treated, thus requiring periodic invasive monitoring. Retinoid compounds which lack this toxicity would be clearly preferred.

Studies by the present applicants using Sprague-Dawley rats confirm literature findings that 13-cis retinoic acid increases serum triglyceride levels. The methods used for showing the triglyceride-inducing effects of retinoids are described in *J. Nutrition*, 110, 343–351, 1980. FIG. 1 shows the comparative effects of 13-cis-retinoic and a RAR-gamma specific retinoid. Orally administered 13-cis-retinoic acid increased serum triglyceride levels by ~350% at 150 mg/kg. The compound of example 1 produced no increase in serum triglycerides at up to 250 mg/kg. Compounds having the beneficial pharmacological effects of retinoids but without retinoid-induced hypertriglyceridemia would be especially desirable for oral retinoid therapy.

The compounds of the present invention can be administered orally, parenterally or topically, depending on such considerations as the condition to be treated, need for site-specific treatment, quantity of drug to be administered, and similar considerations. They are generally used as pharmaceutical compositions with one or more suitable pharmaceutical carriers or diluents conventionally used in pharmaceutical technology.

In the treatment of dermatological conditions, it will generally be preferred to administer the compounds topically, although in certain cases such as treatment of severe acne or psoriasis, oral formulation will be employed. For other indications, parenteral, oral or topical administration may be preferred. The pharmaceutical compositions may be in solid form such as capsules, tablets, powders, gels, salves, ointments, etc. or in liquid form such as solutions, suspensions or emulsions. For parenteral administration, the drug may be prepared in unit dose form in ampules or in multidose containers and may contain additives such as suspending, stabilizing and dispersing agents. The parenteral compositions may be in ready-to-use form or in powder form for reconstitution at the time of delivery with a suitable vehicle such as sterile water. Illustrative examples of suitable pharmaceutical formulations are disclosed, for example, in U.K. 2,164,938A.

The compounds of the present invention may be administered alone or in admixture with other medicaments, e.g. agents for treating skin dryness, providing protection against photoaging, preventing infection, reducing irritation and inflammation, and the like.

The dosages and dosage regimen in which the compounds of the present invention are administered will vary according to the compound, dosage form, mode of administration, the condition being treated and the particulars of the patient being treated. Accordingly, optimal therapeutic concentrations will be best determined at the time of administration by conventional dosage determination procedures. In general, however, the compounds may be administered in amounts of about 0.05 mg to about 5 mg daily per kg of body weight in one or more doses.

Isotretinoin (Accutane®) and etretinate (Tegison®) are used clinically to treat severe recalcitrant cystic acne and severe recalcitrant psoriasis, including the erythrodermica and generalized pustular types, respectively. Their mode of use is amply illustrated in the *Physician's Desk Reference*, 47th Edition, 1993, published by Medical Economics Data. The compounds of the present invention may be administered in a similar fashion to isotretinoin and etretinate according to these guidelines. For treatment of other indications, such as tumors, the compounds of the present invention may be administered to mammals, including humans, in a similar manner to retinoid compounds in the literature which have been shown to be active for such indications.

DESCRIPTION OF SPECIFIC EMBODIMENTS

The specific examples which follow illustrate the synthesis of representative compounds of the present invention and are not to be construed as limiting the scope of the invention. The methods may be adapted to variations in order to produce compounds embraced by this invention but not specifically disclosed.

All temperatures are understood to be in Centigrade (C) when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethylsulfoxide), $D_2O$ (deuterated water), $CDCl_3$ (deuterochloroform) and other conventional deuterated solvents. The infrared (IR) spectral description include only absorption wave numbers (cm$^{-1}$) having functional group identification value.

Preparation of Starting Materials
(1) Synthesis of Ethyl 2-oxo-2(1',2',3',4',-tetrahydro-1',1',4',4'-tetramethyl-6'naphthyl)acetate

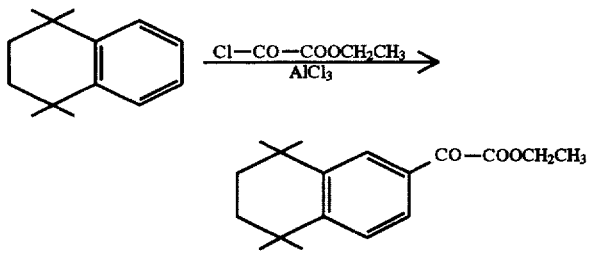

In a 1-liter 3-neck round bottom flask equipped with mechanical stirrer and drying tube were placed 46 ml (55 gms) ethyl oxalyl chloride, 70 gms 1,2,3,4-tetrahydro-1,1,4,4-tetramethylnaphthlene, and 400 ml methylene chloride. To the stirring mixture was added 80 gms AlCl$_3$ portionwise. After complete addition, the mixture was stirred for a further 1½ hours at room temperature, then poured cautiously over 2 L crushed ice. The layers were separated after the ice melted and the aqueous layer was washed with a further 600 ml methylene chloride. The combined organic phases were washed with brine, dried over MgSO$_4$, filtered, evaporated in vacuo, and the resulting oil was vacuum distilled. The main fraction boiled at 131° at 0.14 mmHg. Yield: 84.5 gms (79%) yellow oil.

IR: (NaCl plates) 2963 cm$^{-1}$ (C—H), 1738 cm$^{31}$ $^1$ (ester C=O), 1686 cm$^{-1}$ (ketone C=O), 1206 cm$^{31}$ $^1$ (C—O); NMR: (CDCl$_3$) δ7.99 (d,J=2, 1H, C$_5$—H), 7.71 (d of d, J=8, J=2, 1H, C$_7$—H), 7.44 (d, J=8, 1H, C$_8$—H), 4.45 (q, J=7, 2H, O—CH$_2$), 1.71 (s, 4H, CH$_2$CH$_2$), 1.43 (t, J=7, 3H, ester CH$_3$), s 1.31 and 1.30 (6H each, angular CH$_3$); TLC: (CHCl$_3$/silica) single spot Rf~0.8

(2) Synthesis of 2-Oxo-2(1',2',3',4',-tetrahydro-1',1',4',4',-tetramethyl-6'naphthyl)acetic acid

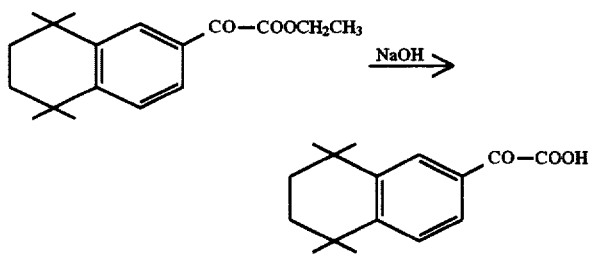

To a solution of 30 gms ethyl 2-oxo-2(1',2',3',4',-tetrahydro-1',1',4',4',-tetramethyl-6'-naphthyl) acetate in 150 ml absolute ethanol was added a solution of 4.76 gms NaOH is 150 ml deionized water. The resulting mixture was stirred at room temperature for 1 hour. The solvent was removed in vacuo and the residue was dissolved in 300 ml water. The aqueous solution was extracted with 100 ml ethyl acetate (which was discarded), then acidified with concentrated hydrochloric acid and the oily product extracted into ethyl acetate. The ethyl acetate was washed with brine, dried over MgSO$_4$, filtered, and evaporated in vacuo to give an orange oil which solidified to a low melting yellow solid upon cooling and scratching. Yield 27.6 gms.

IR: (KBr)broad band 2500–3300 cm$^{-1}$ (acid O—H), 2965 cm$^{-1}$ (C—H), 1742 cm$^{-1}$ (acid C=O), 1680 cm$^{31}$ $^1$ (ketone C=O), 1223 cm$^{-1}$ (C—O ); NMR: (CDCl$_3$) δ8.30 (d, J=2, 1H, C$_5$—H), 8.0 (d of d, J=8, J=2, 1H, C$_7$—H), 7.43 (d, J=8, 1H, C$_8$—H), 1.70 (s, 4H, CH$_2$CH$_2$), 1.30 and 1.29 (s, 6H each angular CH$_3$); TLC: (1% formic acid in 30% ethyl acetate/hexane on silica) single spot Rf~0.3

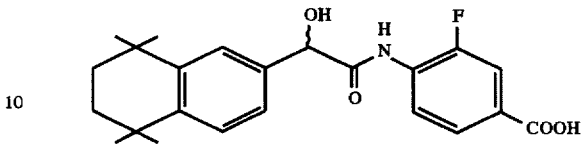

3-Fluoro-4(2'(5",6",7",8"-Tetrahydro-5",5",8", 8"-Tetramethyl-2'-Naphthyl-2'-Naphthyl)-2'-Hydroxy) Acetamidobenzoic Acid 1) 3-Fluoro-4-nitrobenzoic acid

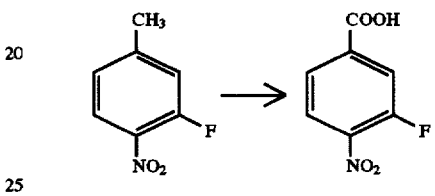

To a mechanically stirred mixture of 10 grams 3-fluoro-4-nitrotoluene, 28.6 grams sodium dichromate and 65 ml water was added dropwise over 1 hour 71 ml concentrated sulfuric acid. The mixture was stirred for an additional hour after complete addition, then diluted with 100 ml water and filtered. The resulting solid was heated gently in 250 ml 2% NaOH solution, cooled, and filtered. The filtrate was acidified with concentrated hydrochloric acid.

The acidified aqueous phase was twice extracted with ethyl acetate. The combined organic phases were washed with saturated NaCl solution, dried over magnesium sulfate, filtered, and evaporated in vacuo to give 8.5 grams 3-fluoro-4-nitrobenzoic acid as a yellow solid, m.p. 168°–170° C.

IR (KBr): 2500–3000 (OH), 1699 (C=O), 1549 and 1356 (NO$_2$), and 1322 (C—F) cm$^{-1}$; NMR (300 MHz): (d$_6$-DMSO) δ7.90 (m, 2H, C$_2$H, C$_6$H), 8.20 (m, 1H, C$_5$H),13.6 (broad s, 1H, COOH); MS: m/z=185

2) Methyl 3-Fluoro-4-nitrobenzoate

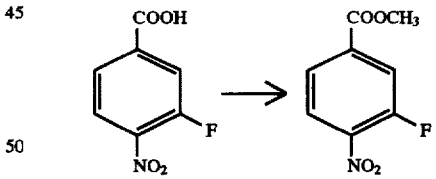

To a solution prepared by the dropwise addition of 12 ml acetyl chloride to 150 ml methanol was added 7.0 grams 3-fluoro-4-nitrobenzoic acid and the resulting mixture was stirred at room temperature for 18 hours. The solvent was removed in vacuo and the residue was partitioned between ethyl acetate and 2% sodium carbonate solution. The organic layer was washed with saturated sodium chloride solution, dried over magnesium sulfate, filtered, and evaporated in vacuo to give 6 gramsof methyl 3-fluoro-4-nitrobenzoate as an orange oil which graduallyhardened to a yellow solid.

IR (KBr): 3067 (C—H), 1732 (C=O), 1526 and 1362 (NO$_2$), and 1287 (C—F) cm$^{-1}$; NMR (300 MHz) (d$_6$-DMSO); δ3.90 (s,3H,CH$_3$), 7.95 (d,J=8.5, of q, J=1.1 and 1.7, 1H, C$_6$H) 8.02 (d,J=11.4, of d,J=1.7,1H, C$_2$H), 8.27 (d,J=8.5, of d, J=7.5, 1H,C$_5$H); MS: m/z=199

3) Methyl 3-Fluoro-4-aminobenzoate

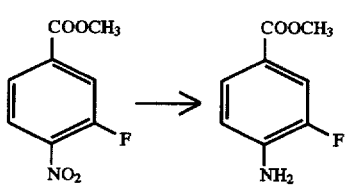

In 150 ml ethyl acetate was dissolved 5.74 grams methyl 3-fluoro-4-nitrobenzoate and the resulting solution was hydrogenated in the Parr apparatus (45 psi) over 600 mg 10% Pd-on-C for about 45 minutes, when the hydrogen uptake ceased. The catalyst was removed by filtration and the solvent was removed in vacuo to give 4.86 grams methyl 3-fluoro-4-aminobenzoate as an off-white solid, m.p. 107°–110° C.

IR (KBr): 3476, 3370(NH), 1690 (C=O), 1620 (C=C), 1304 (C—F) cm$^{-1}$; NMR (300 MHz) (d$_6$-DMSO); δ3.74 (s,3H,CH$_3$), 6.05 (s,2H,NH$_2$), 6.77 (t, J=8.6, 1H, C$_5$H), 7.46 (d,J=11.9, of d, J=1.9, 1H, C$_2$H), 7.50 (d, J=8.3, of d,J=1.9, 1H, C$_6$H); MS: m/z=169

4) Methyl 3-Fluoro-4(2'(5",6",7",8"-tetrahydro-5", 5",8",8"-tetramethyl-2"-naphthyl)-2'-oxo)acetamidobenzoate

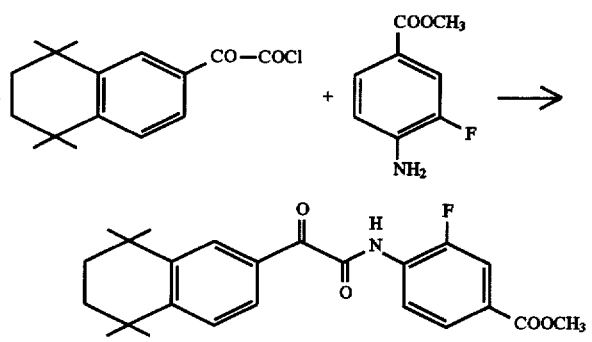

To a solution of the acid chloride from 1.54 grams of 2-oxo-2(1',2',3',4',-tetrahydro-1',1',4',4'-tetramethyl-6'-naphthyl)acetic acid and in 75 ml ethyl acetate was added 1 gram methyl 3-fluoro-4-aminobenzoate and 2.5 ml triethylamine. The resulting solution was then stirred at room temperature for 18 hours. The reaction mixture was then partitioned between ethyl acetate and 2% sodium carbonate solution. All organic phases were combined, washed with saturated sodium chloride solution, dried over magnesium sulfate, filtered, and evaporated in vacuo to give a tan solid. This solid was recrystallized from a mixture of toluene and hexane to give 1 gram of methyl 3-fluoro-4(2'(5",6",7",8", -tetrahydro-5", 5",8",8"-tetramethyl-2"-naphthyl)-2'-oxo) acetamidobenzoate as a light tan solid of m.p. 131°–3°.

IR(KBr): 3351 (NH), 2953 (CH), 1723 (ester C=O), 1703 (ketone C=O), 1559, 1526 (amide C=O), 1290 (C-f) cm$^{-1}$; NMR (300 MHz) (CDCl$_3$: δ1.29 and 1.32 (2s,12H, CH$_3$), 1.7 (s,4H,—CH$_2$CH$_2$—),3.90 (s,3H,OCH$_3$), 7.41 (d, J=8.3,1H,C$_4$H), 7.80 (d,J=11.3, of d,J=1.8, 1H, C$_2$H), 7.88 (d,J=8.6, of d,J=1.1H,C$_6$H), 8.13 (d,J=8.3, of d,J=1.9, 1H, C$_3$H), 8.39 (d, J=1.9, 1H, C$_1$H), 8.58 (t,J=8, 1H, C$_5$H); MS: m/z=411; Elemental analysis: Calculated C 70.06, H 6.37, N 3.40; Found C 70.12, H 6.43, N 3.43

5) Methyl 3-Fluoro-4(2'(5",6",7", 8"-tetrahydro-5",5",7",8"-tetramethyl-2"-naphthyl)-2'-hydroxy)-acetamidobenzoate

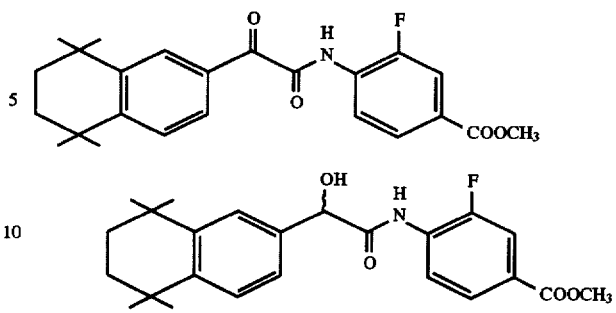

A solution of 750 mg methyl 3-fluoro-4(2'(5",6",7", 8"-tetrahydro-5",5",8",8"-tetramethyl-2"-naphthyl)-2'-oxo)-acetamidobenzoate in a warm mixture of 20 ml methanol and 5 ml ethyl acetate was treated with 34 mg sodium borohydride for 5 minutes, then a few drops concentrated hydrochloric acid was added and the solution was evaporated in vacuo. The residue was partitioned between ethyl acetate and dilute sodium carbonate solution then the aqueous phase was washed with ethyl acetate. The organic phases were combined, washed with saturated sodium chloride solution, dried over magnesium sulfate, filtered, and evaporated in vacuo to give an oil which solidified to a light brown solid, which was recrystallized from a mixture of toluene and hexane to give 590 mg methyl 3-fluoro-4(2'(5",6",7", 8"-tetrahydro-5", 5",8",8"-tetramethyl-2"-naphthyl)-2'-hydroxy) acetamidobenzoate as a light tan solid of m.p. 120°–1°.

IR (KBr): 3366 (OH), 1723 (ester C=O), 1652 and 1530 (amide C=O), 1292 (C—F) cm$^{-1}$; NMR (300 MHz) (CDCl$_3$: δ1.24 (s,6H,C$_5$.(CH$_3$)$_2$), 1.25 (2s,3H,C$_8$.CH$_3$),1.60 (s,4H.CH$_2$CH$_2$), 3.21 (d,J=3,OH), 3.87 (2.3H,OCH$_3$), 5.17 (d,J=3,1H,CHOH), 7.20 (d,J=8.2, of d.J=1.9, 1H, C$_3$,H), 7.31 (d,J=8.2,1H,C$_4$.H),7.38 (d,J=1.9,1H,C$_1$.H),7.73 (d,J=11.3,of d,J=1.8,1H,C$_2$H), 7.79 (d,J=8.6,C$_6$H), 8.44 (t,J=8.1, 1H,C$_5$H),8.76 (d,J=3,1H,NH); MS: m/z=413; Elemental analysis: Calculated C 69.71, H 6.83, N 3.39; Found C 69.81, H 6.84, N 3.44

6) 3-Fluoro-4(2'(5",6",7", 8"-tetrahydro-5",5",8",8"-tetramethyl-2"-naphthyl)-2'-hydroxy) acetamidobenzoic acid

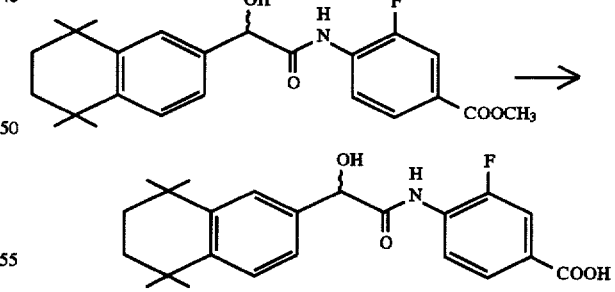

A solution of 242 mg methyl 3-fluoro-4(2'(5",6",7", 8"-tetrahydro-5",5",8", 8"-tetramethyl-2"-naphthyl)-2'-hydroxy)-acetamidobenzoate in 10 ml methanol was treated with 3 ml 1 N sodium hydroxide solution and the resulting mixture was heated in an oil bath at 75°–80° C. for 3 hours, then was cooled and evaporated in vacuo to a syrup. This syrup was partitioned between water and ethyl acetate, the aqueous phase was separated and acidified with concentrated hydrochloric acid and extracted two times with ethyl acetate. The organic phases were combined, washed with saturated sodium chloride solution, dried over magnesium sulfate, filtered, and evaporated to give an off-white solid which was recrystallized from a mixture of ethyl acetate and hexane to give 58 mg 3-fluoro-4(2'(5".6".7". 8"-tetrahydro-5",5",8",8"-tetramethyl-2"-naphthyl)-2'-hydroxy) acetamido-benzoic acid as an off-white solid, m.p. 222.5°–225° C.

IR(KBr): 3414, 3352 (OH), 2550–3000 (COOH), 2959 (CH), 1676 (acid and amide C=O), 1290 (C—F) cm$^{-1}$; NMR (300 MHz) (d$_6$-DMSO); δ1.20 (s,6H,C$_5$.(CH 3)2), 1.21 (s,3H,C$_8$.CH$_3$),1.23 (s,3H,C$_8$.CH$_3$), 1.61 (s,4H, CH$_2$CH$_2$), 5.14 (s,1H,OH), 6.57 (br s, 1H, COOH), 7.19 (d,J=8.2, of d,J=1.7, 1H, C$_3$.H), 7.28 (d,J=8.2, C$_4$.H), 7.43 (d,J=1.6,1H,C$_1$.H), 7.73 (m,2H,C$_2$H and C$_6$H), 8.07 (m,1H, C$_5$H), 9.78 (s,1H,NH); MS: m/z=399; Elemental analysis: Calculated C 69.16, H 6.56, N 3.51; Found C 68.88, H 6.60, N 3.49

The following compounds were prepared by similar methods:

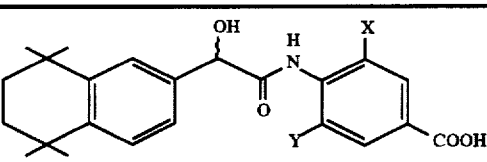

| Example No. | X | Y | M.P. (°C.) | | Analysis (calc) | Analysis (found) |
|---|---|---|---|---|---|---|
| *2 | H | H | 223–225 | C | 71.44 C | 71.48 |
| | | | | H | 7.24 H | 7.22 |
| | | | | N | 3.47 N | 3.62 |
| **3 | CF$_3$ | H | 190–1 (+0.25 ethyl acetate) | C | 64.13 C | 63.96 |
| | | | | H | 5.83 H | 5.86 |
| | | | | N | 3.12 N | 3.06 |
| **4 | OCH$_3$ | H | 214–7 | C | 70.05 C | 69.42 |
| | | | | H | 7.10 H | 7.13 |
| | | | | N | 3.40 N | 3.30 |
| **5 | Br | H | 149–52 | C | 60.01 C | 59.92 |
| | | | | H | 5.69 H | 5.74 |
| | | | | N | 3.04 N | 2.95 |
| | | | | Br | 17.36 Br | 17.28 |
| 6 | Cl | H | 214–5 | C | 66.42 C | 66.52 |
| | | | | H | 6.30 H | 6.34 |
| | | | | N | 3.37 N | 3.31 |
| | | | | Cl | 8.37 Cl | 8.46 |
| 7 | OH | H | 212–7 | C | 69.50 C | 69.49 |
| | | | | H | 6.85 H | 6.89 |
| | | | | N | 3.52 N | 3.51 |

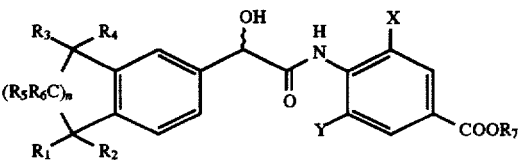

| Example No. | X | Y | M.P. (°C.) | | Analysis (calc) | Analysis (found) |
|---|---|---|---|---|---|---|
| 8 | CH$_3$ | H | 164–6 | C | 72.89 C | 72.70 |
| | | | | H | 7.39 H | 7.54 |
| | | | | N | 3.54 N | 3.42 |
| **9 | CH$_3$ | CH$_3$ | 246–9 | C | 73.32 C | 73.04 |
| | | | | H | 7.63 H | 7.64 |
| | | | | N | 3.42 N | 3.36 |
| **10 | Cl | Cl | 240–1 | C | 61.34 C | 61.13 |
| | | | | H | 5.60 H | 5.68 |
| | | | | N | 3.11 N | 3.02 |
| | | | | Cl | 15.74 Cl | 15.64 |

*literature compound included for comparison
**compound included for comparison

We claim:

1. A method for treating dermatological disorders in a mammal which comprises administering a therapeutically effective amount of a compound of the formula wherein X is F, Cl, OH or CH$_3$, Y is H or F, R$_1$–R$_6$ are each independently hydrogen or C$_1$–C$_6$alkyl, n is an integer of 1 to 4 and R$_7$ is hydrogen or a carboxyl-protecting group, or a pharmaceutically acceptable salt thereof.

2. The method according to claim 1 wherein the dermatological disorder is acne.

3. The method according to claim 1 wherein the dermatological disorder is psoriasis.

4. The method according to claim 1 wherein the dermatological disorder is a premalignant lesion.

5. The method according to claim 1 wherein the dermatological disorder is an actinic keratosis.

* * * * *